(12) United States Patent
Annis

(10) Patent No.: US 8,094,782 B1
(45) Date of Patent: Jan. 10, 2012

(54) X-RAY BACKSCATTER SYSTEM FOR IMAGING SOFT TISSUE REGIONS

(76) Inventor: Martin Annis, Cambridge, MA (US)

( * ) Notice: Subject to any disclaimer, the term of this patent is extended or adjusted under 35 U.S.C. 154(b) by 0 days.

(21) Appl. No.: 13/032,572

(22) Filed: Feb. 22, 2011

Related U.S. Application Data

(60) Provisional application No. 61/338,547, filed on Feb. 22, 2010.

(51) Int. Cl.
G01N 23/203 (2006.01)
G01N 23/201 (2006.01)

(52) U.S. Cl. .................. 378/87; 378/37; 378/86

(58) Field of Classification Search .......... 378/37, 378/70, 86, 87, 146–151, 210
See application file for complete search history.

(56) References Cited

U.S. PATENT DOCUMENTS

| | | | |
|---|---|---|---|
| 4,809,312 A * | 2/1989 | Annis ........................ | 378/146 |
| 4,839,913 A * | 6/1989 | Annis et al. ................ | 378/44 |
| 5,692,029 A | 11/1997 | Husseiny et al. | |
| 7,136,453 B2 | 11/2006 | Jupp et al. | |
| 7,561,666 B2 | 7/2009 | Annis | |
| 7,620,150 B1 | 11/2009 | Annis | |
| 2005/0185756 A1* | 8/2005 | Wang et al. ............... | 378/37 |
| 2007/0098142 A1 | 5/2007 | Rothschild et al. | |

* cited by examiner

*Primary Examiner* — Anastasia Midkiff
(74) *Attorney, Agent, or Firm* — Altman & Martin; Steven K Martin

(57) ABSTRACT

An x-ray source emits a cone beam a rapidly rotating, x-ray-opaque disc with four narrow radial slots. The slots break the cone beam into fan beams that are emitted to an x-ray-opaque plate with a narrow slit. As each fan beam moves across the plate, the slit produces a scanning x-ray pencil beam. The backscatter detector is mounted adjacent to the plate and has a slightly larger slit that is aligned with the plate slit. The pencil beam enters the object space through the detector slit. The pencil beam moves rapidly in a line across the object space, 20 cm in 0.1 second. Simultaneously, the assemblage of x-ray source, disc, plate, and detector moves slowly in the x direction at 1 mm in 0.05 second. Thus, the raster scan of the 20 cm×20 cm region is accomplished in 10 seconds.

9 Claims, 4 Drawing Sheets

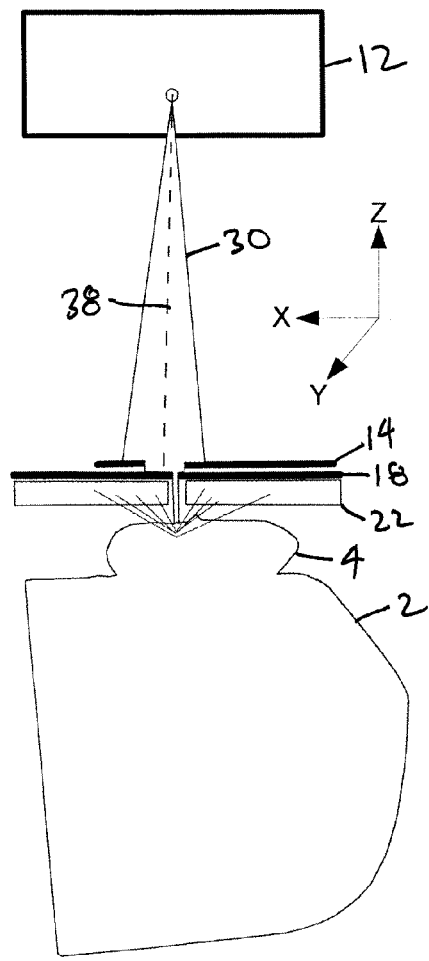
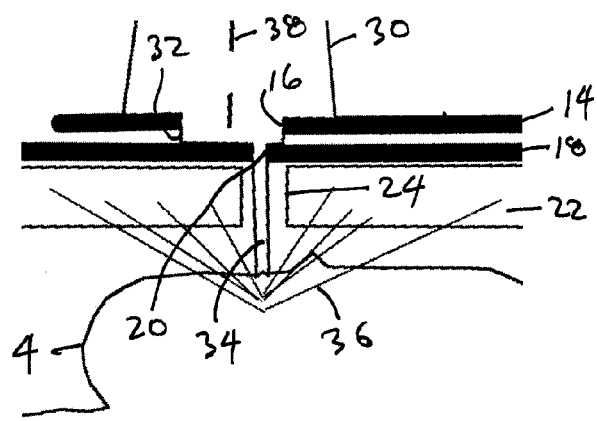
FIG. 3
FIG. 2

X-RAY BACKSCATTER SYSTEM FOR IMAGING SOFT TISSUE REGIONS

CROSS-REFERENCES TO RELATED APPLICATIONS

The present application claims the benefit of and priority to U.S. Provisional Patent Application No. 61/338,547, filed on Feb. 22, 2010 for title X-RAY BACKSCATTER SYSTEM FOR IMAGING THE BREAST, LYMPH NODES, LUNGS, HEART AND OTHER SOFT TISSUE REGIONS in the name of Martin Annis, and is hereby incorporated by reference in its entirety.

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING COMPACT DISK APPENDIX

Not Applicable

BACKGROUND OF THE INVENTION

1. Field of the Invention

The present invention relates to x-ray imaging, more particularly, to backscatter x-ray imaging of soft body tissue.

2. Description of the Related Art

X-ray imaging has been done by conventional transmission x-rays for many years. Film imaging has now been largely replaced by digital imaging. This more convenient mode does not produce better spatial resolution but is superior in allowing convenient transmission of the images and manipulation to better evaluate the images.

Still more recent is the development of three-dimensional (3D) systems for breast imaging. These systems use digital tomography/laminography algorithms that produce 3D images that appear at the present time to be better able to detect small cancers of the breast.

Thermal (infrared) imaging of the breast has a long history. It has recently been proposed to use nano-particles that have been tagged to locate tumor tissue together with external magnetic field excitation to locally heat suspect areas in the breast for imaging and treatment.

The use of backscatter x-ray systems for the inspection of personnel for security purposes is now common. These systems operate at very low exposure levels and are limited to an exposure of 10 micro-Roentgens (μR) by government regulation. The current system will provide more than 1000 times greater x-ray flux to the patient than the security systems, providing image quality never seen before in soft tissue or the lung.

BRIEF SUMMARY OF THE INVENTION

The purpose of the present invention is to provide a more efficient method of detecting early stages of cancer and other diseases. Current procedures have about 10 to 20 percent false positive and full negative results. In addition, the invention is more user-friendly to the patient because it does not require compressing the breast of the patient. It also reduces the radiation exposure to the patient.

In the present system, an x-ray source emits a cone beam a rapidly rotating, x-ray-opaque disc with four narrow radial slots. The slots break the cone beam into moving fan beams that are emitted to an x-ray-opaque plate with a narrow slit. As each fan beam moves across the plate, the slit produces a scanning x-ray pencil beam. The backscatter detector is mounted adjacent to the plate and has a slightly larger slit that is aligned with the plate slit. The pencil beam enters the object space through the detector slit.

The area of the object space is 20 cm×20 cm because this is the area of larger breasts. The distance from the x-ray source to the rotating disc/plate is at least 30 cm to ensure that the angle of the pencil beam 34 is always nearly vertical. The size of the pencil beam is a compromise. A larger pencil beam produces more x-ray flux, but a smaller pencil beam produces better spatial resolution. A 2 mm×2 mm beam is chosen and sampled twice in both directions to achieve 1 mm×1 mm pixels.

The pencil beam moves very rapidly in a line across the length of the object space in the y direction, 20 cm in 0.1 second. Simultaneously, the entire assemblage of x-ray source, disc, plate, and detector moves slowly in the x direction at 1 mm in 0.05 second. The x-rays scattered backwards from the pencil beam are received by the detector. The appropriate detector pixel locations are sampled 200 times during each y passage of the pencil beam. Thus, the raster scan of the 20 cm×20 cm region is accomplished in 10 seconds, sampling 200×200=40,000 pixels. The detector converts these backscattered x-rays into a line signal for each line scanned by the pencil beam. A processor converts the line signals into line images and the line images into a complete image using any one of a number of algorithms known in the art.

The useful imaging depth of the backscatter imaging system of the present invention is about 5 cm, which is about the thickness of the compressed breast. For the chosen x-ray peak energy of 150 keV, the difference in contrast between the front of the breast and the back of the breast only differs by a factor of 7. There is not a major difference in the efficiency of the x-ray imaging as the peak energy of the x-ray beam changes from 70 keV to 100 keV to 150 keV. This is in contrast to existing transmission x-ray mammography systems that must operate at about 25 keV peak x-ray energy.

In backscatter imaging, the detector is not behind the patient. It allows the compression of the breast against the chest using the weight of the patient or a cloth or other wrap around the patient to bind the breast against the patient's body. This does away with the need of a breast compression device.

The present invention can also be used to produce three-dimensional tomography images. After an x-ray backscatter image is produced with the x-ray source in the central position relative to the disc slots/plate slit, another backscatter image is produced after moving the x-ray source to at least one other position significantly off-center. Preferably, four other positions are used, thereby producing five backscatter images of the object. These five images are combined by any one of a number of well-known algorithms to produce digital tomography images of "slices" parallel to the surface of the object at different depths within the object being scanned.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein:

FIG. 2 is an upside down, side cross-sectional view of the system of FIG. 1;

FIG. 3 is n expanded view of the pencil beam generating components of FIG. 2;

DETAILED DESCRIPTION OF THE INVENTION

Figure 1:
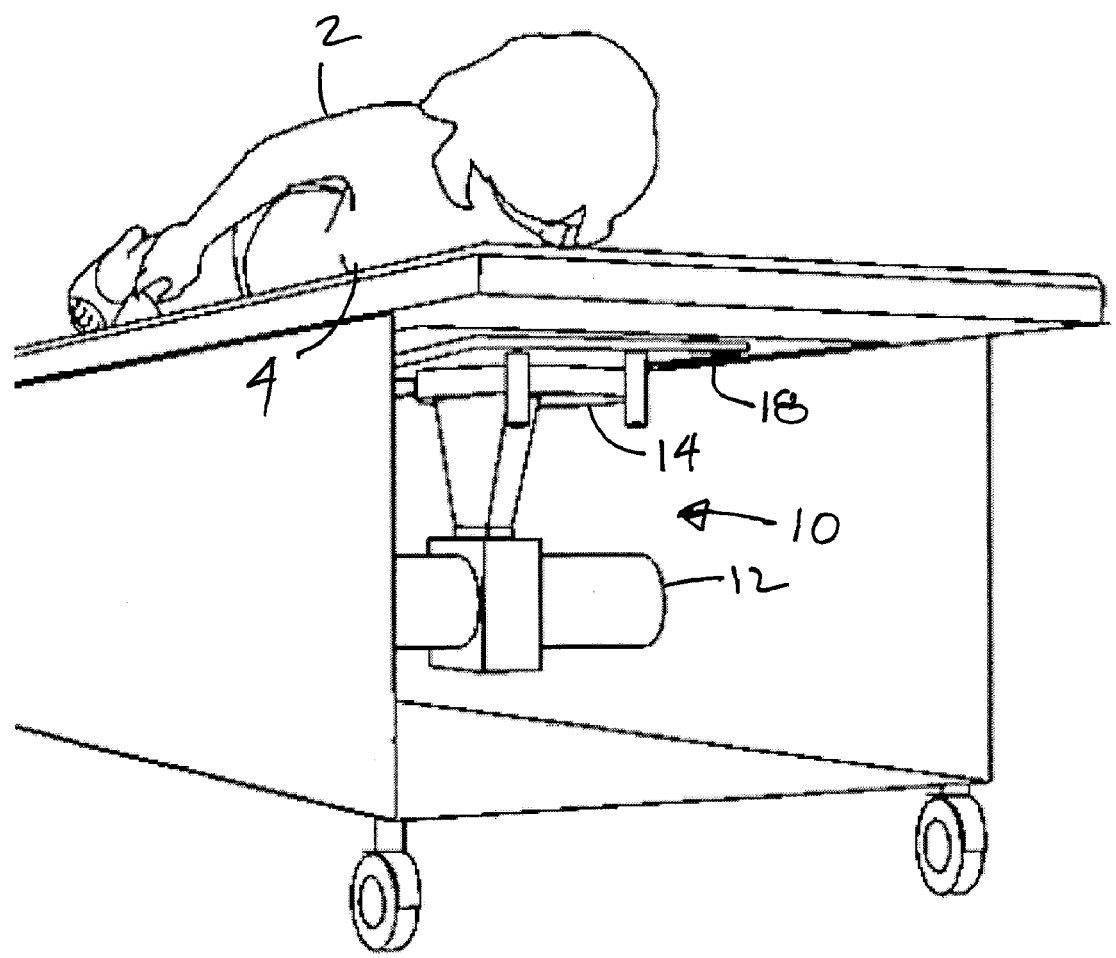
FIG. 1 is a perspective view of a system in use incorporating the present invention.
Figure 4:
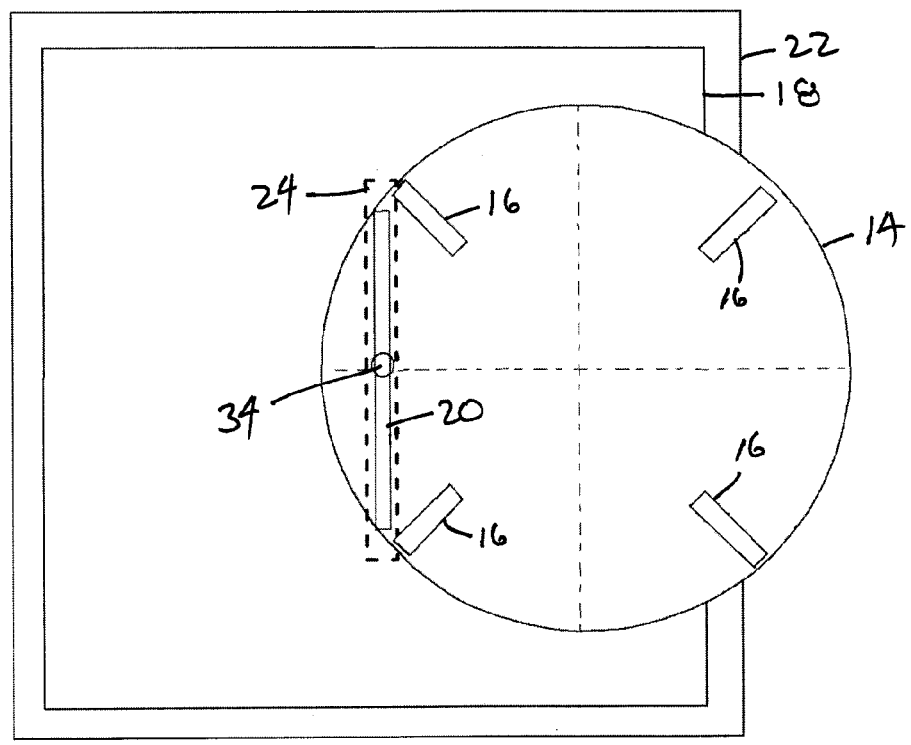
FIG. 4 is a view of the major components of the system of FIG. 1 as viewed from the x-ray source.

U.S. Pat. No. 7,620,150, issued to the present inventor and entitled X-ray Backscatter System for Imaging at Shallow Depths, discloses a method of producing images using a backscatter system and is incorporated herein by reference. The method of the present invention is an improved version of the previous patent and differs from the previous patent in several ways. The previous patent is limited to small area regions and shallow depths within those regions. The present invention achieves the goal of examining a larger area without losing efficiency of detection at the edges of the images by moving the long narrow slit in the backscatter detector transversely along with the transverse motion of the long narrow slit in the pencil beam generator. The greatly increased penetration of x-rays is accomplished by using a much higher power (Watts) and energy (keV) x-ray source, as described in detail below. The choice of 150 keV peak energy for mammography is a major increase over current systems which use about 15 to 20 keV energy. They require this lower energy to achieve the contrast needed to detect lesions. However, this reduces the efficiency of these systems because of the absorption and scattering of x-rays of this low energy. The high peak energy used here allows greater penetration, and scattering does not affect the spatial resolution since this is totally determined by the pencil beam diameter.

In backscatter imaging, it is not necessary to have a detector behind the patient. For the breast this is very convenient since it allows the compression of the breast against the chest, which is a far more comfortable arrangement than in current systems. Using the weight of the patient or using a cloth or other wrap around the patient to bind the breast against the patient's body to compress the breast(s), thus doing away with the need of a breast compression device, is another feature of the invention. Neither of these ideas can be implemented in current systems because they must use a detector array directly on the other side of the breast.

The current invention has intrinsically lower spatial resolution than the prior art and is thus not capable of detecting the small micro-calcifications sometimes but not always accompanying cancer lesions. Current systems, not efficient in seeing the soft tissue cancers lean heavily on the detection of these micro-calcifications. However, all cancers have a soft tissue component and this is definitive in the diagnosis. Thus the ability to clearly image tumors as smaller than 1 cm in size and even image the density variation within the tumor is a major advance in breast cancer detection and eventually, treatment.

Backscatter imaging uses a single narrow pencil beam (and a very wide solid angle of acceptance detector of the backscattered photons) which can be shown to be the most efficient design. This most efficient design however is not very efficient in the fraction of photons used compared to other x-ray systems, so the highest power x-ray tubes available are used. This is a very important feature of the current invention, and not in the prior art. The ability to detect a soft tissue tumor using x-rays depends (1) on the density and elemental composition of the tissue being examined and (2) on the number of x-ray photons available in the x-ray beam.

The separation of normal soft tissue and tumor soft tissue is determined by the mass absorption coefficients of the two materials. Since cancer tissue has the same elemental composition as normal tissue, the separation of the two materials is only in the different mass attenuation coefficients of the materials, i.e. mainly the density. The compositions of various human tissues according to National Institute of Standards and Technology (NIST) data and taken from Stephen M. Seltzer, *Calculation of Photon Mass Energy-Transfer and Mass Energy-Absorption Coefficients*, 136 Radiation Research, November 1993, at 147-170 are shown in Table I.

TABLE I

| Material | Density (g/cm$^3$) | Composition (Z: fraction by weight) |
|---|---|---|
| Breast Tissue | 1.020 | 1: 0.106000 |
| | | 6: 0.332000 |
| | | 7: 0.030000 |
| | | 8: 0.527000 |
| | | 11: 0.001000 |
| | | 15: 0.001000 |
| | | 16: 0.002000 |
| | | 17: 0.001000 |
| Soft Tissue | 1.060 | 1: 0.102000 |
| | | 6: 0.143000 |
| | | 7: 0.034000 |
| | | 8: 0.708000 |
| | | 11: 0.002000 |
| | | 15: 0.003000 |
| | | 16: 0.003000 |
| | | 17: 0.002000 |
| | | 19: 0.003000 |
| Whole Blood | 1.060 | 1: 0.102000 |
| | | 6: 0.110000 |
| | | 7: 0.033000 |
| | | 8: 0.745000 |
| | | 11: 0.001000 |
| | | 15: 0.001000 |
| | | 16: 0.002000 |
| | | 17: 0.003000 |
| | | 19: 0.002000 |
| | | 26: 0.001000 |

The data indicates a difference in density between blood and breast tissue of about 1.060/1.020, or 4%. So it is not unreasonable to expect that tumor tissue may be more dense than normal breast tissue by about 1% due to the elevated amount of blood characteristic of tumor tissue relative to normal breast tissue and also the higher concentration of higher Z elements in blood that increase the mass attenuation coefficient of blood. This 1% increase in the difference in x-ray attenuation is apparently what is seen in current mammography images of soft tissue tumors.

The separation by difference in density of normal soft tissue from tumor tissue is detected only if there is sufficient incident flux. Thus, to observe the small separation in the density and mass absorption coefficients of the normal and tumor tissue there must be sufficient x-ray photons per backscattered pixel to establish a standard deviation in the number of photons detected that is small compared to the separation in the attenuation of the x-rays by the tumor and normal tissue. This requires a large incident flux and hence a powerful x-ray source, which only a rotating anode x-ray tube can provide. This is a feature of the invention, since no prior art has used this in backscatter imaging.

Described in detail below is the use of the present invention for imaging of soft tissue breast tumors. However, the system of the present invention may also be used for other applications including, but not limited to, the imaging of soft tissue tumors of the lung and imaging of a beating heart.

It is known that lung lesions that are calcified are less likely to be cancer than soft tissue lesions in the lung. Backscatter imaging is uniquely sensitive to this difference because the calcium in the lesions produces very much greater x-ray attenuation than a soft tissue lesion of the same volume.

For imaging of the heart to a depth of about five cm from the front or back of the patient, backscatter offers great advantages over CT, transmission imaging, and MRI imaging, all of which are too slow to image a beating heart. The present invention uses a rapidly moving pencil beam of x-rays that "stops" the heart motion. Thus, the image is not blurred, but rather records the motion of the beating heart and the larger blood vessels.

A system for use by the present invention is shown in the FIGS. 1-4. The scan is achieved by using the same technique now widely used to produce a pencil beam of x-rays that scans the xy plane. An x-ray source 12 emits a cone beam 30 with an axis 38 to an x-ray-opaque disc 14 with four narrow radial slots 16 that rotates rapidly perpendicularly to the cone beam axis 38. The slots 16 break the cone beam 30 into moving fan beams 32. The disc 14 is mounted adjacent to an x-ray-opaque plate 18 with a narrow slit 20. The moving fan beams 32 impinge on the plate 18 and, as each fan beam 32 moves across the plate 18, the stationary slit 20 in the plate 18 produces a scanning x-ray pencil beam 34.

The backscatter detector 22 is mounted adjacent to the plate 18 and has a slightly larger slit 24 that is aligned with the plate slit 20. The pencil beam 34 enters the object space 26 through the detector slit 24 without entering the backscatter detector 22 on its way into the object space 26. The object space 26 is where the object being imaged resides and, in the remainder of the present specification, the object being imaged is a female breast 4.

The total area of the object space 26 chosen to be scanned by the pencil beam 34 is 20 cm×20 cm, because this is the area of larger breasts. The distance from the x-ray source 12 to the rotating disc 14/plate 18 is at least approximately 30 cm to ensure that the angle of the pencil beam 34 is always nearly vertical while the pencil beam 34 moves rapidly over the object space 26. In the illustrated embodiment, the maximum angle from the normal to the slit 20 is +/−(10 cm)/(30 cm)=0.33 radians=19°. Since the ratio of the slant distance into the object space 26 is proportional to the cos(19°)=0.945, this is not a big effect.

The size of the pencil beam 34 is a compromise because a larger pencil beam produces more x-ray flux, which is desirable, and a smaller pencil beam produces better spatial resolution, also desirable. A 2 mm×2 mm beam is chosen and sampled twice in both directions, using the Nyquist Theorem, to achieve 1 mm×1 mm pixels. Since the smallest lesions currently seen are about 10 mm in diameter, this resolution will detect and image very small lesions.

The pencil beam 34 moves very rapidly in a line across the length of the object space 26 in the y direction as each of the four radial slots 16 in the rotating disc 14 crosses over the slit 20 in the plate 18, 20 cm in 0.1 second. Simultaneously, the entire assemblage 10 of x-ray source 12, disc 14, plate 18, and detector 22 moves slowly in the x direction across the width of the object space 26 at 1 mm in 0.05 second or 20 cm in 10 seconds. So, the pencil beam 34 translates by 1 mm in the x direction while it moves 20 cm in the y direction. Thus, the raster scan of the 20 cm×20 cm region is accomplished in 10 seconds. Also, the line that the pencil beam traces across the length of the object space 26 is not quite parallel to the y axis, but is at an angle arctan(1 mm/200 mm)=0.28°, which is considered by the present invention to be generally orthogonal to the x direction.

As the pencil beam 34 scans the breast 4, x-rays are scattered by the breast tissue. Those x-rays 36 that are scattered backwards from the pencil beam 34 and penetrate the breast 4, impinge on and are received by the detector 22. The appropriate detector pixel locations are sampled 200 times (i.e., twice for each passage of the 2 mm pencil beam 34 over each pixel location, using the Nyquist theorem to double the spatial resolution) during each y passage of the pencil beam 34. The raster scan of the 20 cm×20 cm region is accomplished in 10 seconds, sampling 200×200=40,000 pixels.

The backscatter detector 22 is described below and is designed to be large enough to detect the vast majority of the x-rays 36 that are scattered backward and penetrate the breast 4 in the backward direction. The detector 22 converts these backscattered x-rays 36 into a line signal for each line scanned by the pencil beam 34. A processor converts the line signals into line images and the line images into a complete image using any one of a number of algorithms known in the art.

Figure 6:
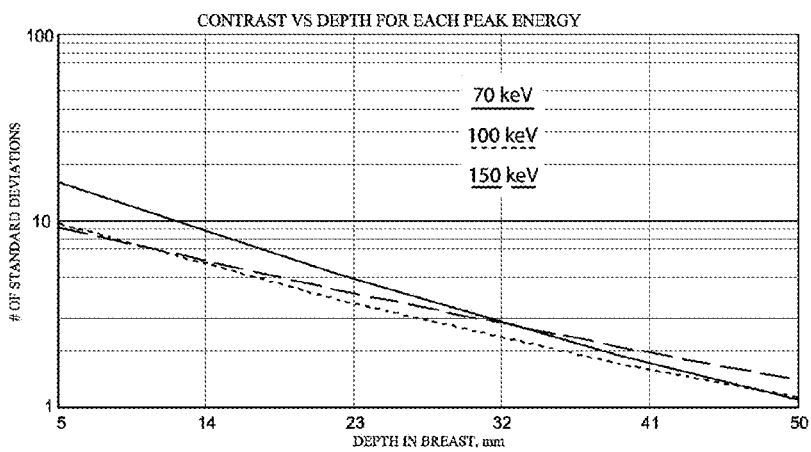
FIG. 6 is a graph showing the efficiency of the x-ray imaging as a function of depth.

As will be shown below, the useful imaging depth of the backscatter imaging system of the present invention is about 5 cm, which is about the thickness of the compressed breast 4. For the x-ray peak energy chosen for the example, 150 keV, the difference in contrast between the front of the breast and the back of the breast only differs by a factor of 7. FIG. 6 shows that there is not a major difference in the efficiency of the x-ray imaging as a function of depth as the peak energy of the x-ray beam changes from 70 keV to 100 keV to 150 keV. Below 70 keV peak, however, the penetration efficiency of the system decreases rapidly, and below 50 keV the penetration is not sufficient to image a 5 cm thick breast. This is in marked contrast to existing transmission x-ray mammography systems that must operate at about 25 keV peak x-ray energy.

A major limitation to the spatial resolution of transmission x-ray systems is the scattering of the primary beam as it penetrates the breast. The fraction of scattered x-rays to the non-scattered x-rays (the only useful rays in the image) can be more than a factor of 2 for a beam of 30 keV peak at a breast thickness of approximately 5 cm, resulting in a loss of contrast and spatial resolution.

The performance of the pencil beam backscatter system of the present invention is calculated below. The system of the present invention is optimized to allow the most efficient use of the x-rays emitted by the x-ray source. The calculation assumes parameters that can be simply changed from those chosen values in order to optimize the design.

With the superior intrinsic imaging efficiency of backscatter imaging near the surface of an object, it is possible to see details of tumors that have never before been seen. For the first time, the soft tissue is imaged in x-rays with a contrast efficiency two orders of magnitude better than any previous system.

The following parameters have been chosen to illustrate the present invention. They may be changed without changing the thrust of the invention. The peak x-ray energies of 70 keV, 100 keV and 150 keV are used. Throughout the remainder of the present specification, when 70, 100, and 150 is a suffix or elsewhere in a variable name, it refers to a system where the peak x-ray energy from the x-ray source is 70 keV, 100 keV, and 150 keV, respectively. The cross-section of the scanning x-ray pencil beam is assumed to be 2 mm×2 mm. Double sampling in two directions, using the Nyquist theorem, results in a spatial resolution, or pixel size, of approximately 1 mm.

Z is the atomic number of low Z elements that form human tissue.

W is the atomic weight of an element, in g/atomic weight.

Y=½ is the ratio Z/W and is assumed constant.

μe is the cross-sectional area per electron for all elements for backward scattering, in cm²/electron.

$A = 6 \times 10^{23}$ is Avogadro's number, in atoms/atomic weight.

Ne=Y×A is the number of electrons/g for each material.

Dph=0.2 cm is the linear dimension of the pin hole and Dpix=Dph/2 cm=0.1 cm is the corresponding side of a pixel. Apix=Dpix²=0.01 cm² is the area of a pixel. The pencil beam cross-sectional area is twice the area of a pixel because the Nyquist theorem applies in both scan directions, x and y.

The size of the projected x-ray source in the tumor, dprojx, due to the demagnification of the x-ray source diameter is the diameter of the x-ray source, dx, times the ratio of the distance from the plate slit 20 to the soft tissue, Dtumor, divided by the distance from the plate slit 20 to the source, Dsource. If dx=3 mm, Dtumor=5 cm, and Dsource=30 cm, then dprojx=dx× (Dtumor/Dsource)=0.5 mm or about ½ the pixel dimension. Thus, the pencil beam diameter of 2 mm is not affected much due to the x-ray source size.

Figure 7:
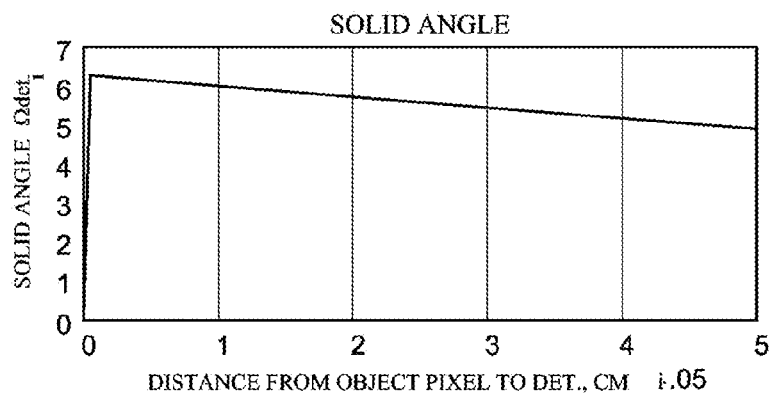
FIG. 7 is a graph showing that the solid angle Qdet, is rather constant at a value of approximately 5.5 steradians over all depths to 5 cm.

The solid angle subtended by the backscatter detector 22 at an average location in the tumor, Ωdet, is calculated as:

$$\Omega det_j = 4 \cdot \left[ \int_0^a \int_0^b \frac{z_i}{[x^2 + y^2 + (z_i)^2]^{\frac{3}{2}}} dx\,dy \right]$$

where i=0 . . . 100, $z_i$=0.05i, a=20 cm, and b=20 cm. a and b are one half of the lateral dimensions of the flat backscatter detector 22 and z is the perpendicular distance from a point in the tumor to the face of the detector 22. A graph of $\Omega det_i$ is shown in FIG. 7, which shows that the solid angle is rather constant at a value of approximately 5.5 steradians over all depths to 5 cm.

The total solid angle, Ωtot, subtended by the scattering voxel is about 5.5 steradians. This solid angle is divided into 10 equal-sized portions, Ωfix, that measure the distance Xrs from this voxel along the corresponding slant angle of the solid angle up to the surface of the backscatter detector. Θs is the slant angle between the normal to the surface of the detector and the line from the voxel to the surface for the particular solid angle defined by s=0 . . . 9 and is calculated as:

$$\theta_s = a\sin\left[\frac{(s+1) \cdot \Omega fix}{2 \cdot \pi}\right]$$

Xnorm, Xslant, and Xslanttum are the thicknesses of material (measured in the standard way) between the chosen voxel and the surface of the backscatter detector. Since the x-ray source is relatively far from the pin hole and thus the angle with the normal to the plane of the detector is small, it is assumed that the incident pencil beams are vertical.

Shown below are the thicknesses (g/cm²) used in the calculation. The density of the tumor, denstumor, is assumed to be 1% different from normal breast tissue. With r=0 . . . 74, ρtum=1+ftum=1.01, and ftum=0.01, where ptum is the density of the tumor in g/cm³ and ftum is the fractional difference in density from normal tissue.

$$Xnorm_r := .1 \cdot r \quad Xtum_r := Xnorm_r \cdot \rho tum$$

$$Xslant_{r,s} := \frac{Xnorm_r}{\cos(\theta_s)} \quad Xslanttum_{r,s} := \frac{Xtum_r}{\cos(\theta_s)}$$

since the path back to the detector is nearly always through normal tissue.

The three matrices below show the normalized photon spectra of the x-ray source for 70 keV, 100 keV, and 150 keV. The second column shows the energy in MeV, and the first column is the relative number of photons in the energy interval of 0.007 MeV for the 70 keV x-ray source, 0.01 MeV for the 10 keV x-ray source, and 0.015 MeV for the 150 keV x-ray source.

$$M70 := \begin{pmatrix} 1 & .007 \\ .67 & .014 \\ .55 & .021 \\ .47 & .028 \\ .4 & .035 \\ .33 & .042 \\ .25 & .049 \\ .18 & .056 \\ .11 & .063 \\ .03 & .070 \end{pmatrix} \quad M100 := \begin{pmatrix} 1 & .01 \\ .67 & .02 \\ .55 & .03 \\ .47 & .04 \\ .4 & .05 \\ .33 & .06 \\ .25 & .07 \\ .18 & .08 \\ .11 & .09 \\ .03 & .1 \end{pmatrix} \quad M150 := \begin{pmatrix} 1 & .015 \\ .67 & .030 \\ .55 & .045 \\ .47 & .060 \\ .4 & .075 \\ .33 & .09 \\ .25 & .105 \\ .18 & .120 \\ .11 & .135 \\ .03 & .15 \end{pmatrix}$$

Using data from the NIST, Table II shows the mass attenuation coefficient, patt, in column two and the mass absorption coefficient, μabs, in breast tissue in column three for x-rays of the energies (MeV) shown in column one.

TABLE II

| Energy (MeV) | μatt (cm²/g) | μabs (cm²/g) |
|---|---|---|
| $1.00000 \times 10^{-3}$ | $3.263 \times 10^3$ | $3.255 \times 10^3$ |
| $1.03542 \times 10^{-3}$ | $2.975 \times 10^3$ | $2.967 \times 10^3$ |
| $1.07210 \times 10^{-3}$ | $2.710 \times 10^3$ | $2.703 \times 10^3$ |
| $1.07210 \times 10^{-3}$ | $2.716 \times 10^3$ | $2.709 \times 10^3$ |
| $1.50000 \times 10^{-3}$ | $1.088 \times 10^3$ | $1.085 \times 10^3$ |
| $2.00000 \times 10^{-3}$ | $4.842 \times 10^2$ | $4.825 \times 10^2$ |
| $2.14550 \times 10^{-3}$ | $3.961 \times 10^2$ | $3.946 \times 10^2$ |
| $2.14550 \times 10^{-3}$ | $3.983 \times 10^2$ | $3.967 \times 10^2$ |
| $2.30297 \times 10^{-3}$ | $3.250 \times 10^2$ | $3.235 \times 10^2$ |
| $2.47200 \times 10^{-3}$ | $2.649 \times 10^2$ | $2.636 \times 10^2$ |
| $2.47200 \times 10^{-3}$ | $2.686 \times 10^2$ | $2.670 \times 10^2$ |
| $2.64140 \times 10^{-3}$ | $2.221 \times 10^2$ | $2.204 \times 10^2$ |
| $2.82240 \times 10^{-3}$ | $1.831 \times 10^2$ | $1.818 \times 10^2$ |
| $2.82240 \times 10^{-3}$ | $1.845 \times 10^2$ | $1.831 \times 10^2$ |
| $3.00000 \times 10^{-3}$ | $1.546 \times 10^2$ | $1.533 \times 10^2$ |
| $4.00000 \times 10^{-3}$ | $6.625 \times 10^1$ | $6.540 \times 10^1$ |
| $5.00000 \times 10^{-3}$ | $3.407 \times 10^1$ | $3.341 \times 10^1$ |
| $6.00000 \times 10^{-3}$ | $1.972 \times 10^2$ | $1.918 \times 10^2$ |
| $8.00000 \times 10^{-3}$ | $8.320 \times 10^0$ | $7.899 \times 10^0$ |
| $1.00000 \times 10^{-2}$ | $4.295 \times 10^0$ | $3.937 \times 10^0$ |
| $1.50000 \times 10^{-2}$ | $1.378 \times 10^0$ | $1.094 \times 10^0$ |
| $2.00000 \times 10^{-2}$ | $6.889 \times 10^{-1}$ | $4.394 \times 10^{-1}$ |
| $3.00000 \times 10^{-2}$ | $3.403 \times 10^{-1}$ | $1.260 \times 10^{-1}$ |
| $4.00000 \times 10^{-2}$ | $2.530 \times 10^{-1}$ | $5.792 \times 10^{-2}$ |
| $5.00000 \times 10^{-2}$ | $2.186 \times 10^{-1}$ | $3.666 \times 10^{-2}$ |

TABLE II-continued

| Energy (MeV) | μatt (cm²/g) | μabs (cm²/g) |
|---|---|---|
| $6.00000 \times 10^{-2}$ | $2.006 \times 10^{-1}$ | $2.881 \times 10^{-2}$ |
| $8.00000 \times 10^{-2}$ | $1.808 \times 10^{-1}$ | $2.470 \times 10^{-2}$ |
| $1.00000 \times 10^{-1}$ | $1.688 \times 10^{-1}$ | $2.478 \times 10^{-2}$ |
| $1.50000 \times 10^{-1}$ | $1.493 \times 10^{-1}$ | $2.734 \times 10^{-2}$ |
| $2.00000 \times 10^{-1}$ | $1.361 \times 10^{-1}$ | $2.945 \times 10^{-2}$ |
| $3.00000 \times 10^{-1}$ | $1.179 \times 10^{-1}$ | $3.173 \times 10^{-2}$ |
| $4.00000 \times 10^{-1}$ | $1.055 \times 10^{-1}$ | $3.260 \times 10^{-2}$ |
| $5.00000 \times 10^{-1}$ | $9.631 \times 10^{-2}$ | $3.281 \times 10^{-2}$ |

The data in Table II is used to construct the following matrices:

$$\mu att70 := \begin{pmatrix} 7 & 14 \\ 14 & 2.2 \\ 21 & .68 \\ 28 & .41 \\ 35 & .29 \\ 42 & .22 \\ 49 & .22 \\ 56 & .21 \\ 63 & .20 \\ 70 & .19 \end{pmatrix} \quad \mu att100 := \begin{pmatrix} 10 & 4.32 \\ 20 & .69 \\ 30 & .34 \\ 40 & .25 \\ 50 & .22 \\ 60 & .20 \\ 70 & .19 \\ 80 & .18 \\ 90 & .17 \\ 100 & .17 \end{pmatrix} \quad \mu att150 := \begin{pmatrix} 15 & 1.4 \\ 30 & .34 \\ 45 & .23 \\ 60 & .2 \\ 75 & .19 \\ 90 & .17 \\ 105 & .16 \\ 120 & .16 \\ 135 & .15 \\ 150 & .15 \end{pmatrix}$$

$$\mu abs70 := \begin{pmatrix} 7 & 13 \\ 14 & 2 \\ 21 & .42 \\ 28 & .16 \\ 35 & .1 \\ 42 & .053 \\ 49 & .040 \\ 56 & .032 \\ 63 & .028 \\ 70 & .027 \end{pmatrix} \quad \mu abs100 := \begin{pmatrix} 10 & 3.9 \\ 20 & .44 \\ 30 & .13 \\ 40 & .06 \\ 50 & .04 \\ 60 & .03 \\ 70 & .027 \\ 80 & .025 \\ 90 & .025 \\ 100 & .025 \end{pmatrix} \quad \mu abs150 := \begin{pmatrix} 15 & 1.1 \\ 30 & .13 \\ 45 & .05 \\ 60 & .03 \\ 75 & .026 \\ 90 & .025 \\ 105 & .025 \\ 120 & .025 \\ 135 & .026 \\ 150 & .027 \end{pmatrix}$$

μbs is the absorption of the backscattered rays on their way out of the breast into the large backscatter detector. The x-rays that are initially scattered from the narrow pencil beam are sometimes scattered backwards toward the x-ray source penetrating the breast and enter the backscatter detector and sometimes may be emitted in the forward direction and thus not detected. They may also be absorbed via the photoelectric effect and removed. They may also be scattered again and again sometimes ending in the detector. In the absence of any absorption, more than half of the x-rays will end up in the detector. In order to calculate this effect accurately, it would be necessary to perform a Monte Carlo calculation, following many photons as they traverse the object. For the present, a conservative method of estimating this probability is used. It is assumed that if a photon backscattered from the incident pencil beam suffers either an additional scattering or an absorption event on the way back from the chosen voxel in the pencil beam to the detector, the photon does not reach the detector, i.e., μbs=μatt which is always larger than μabs. This is conservative because such a photon has a good probability of reaching the detector after being scattered once.

$$\mu abs70 := \begin{pmatrix} 7 & 14 \\ 14 & 2.2 \\ 21 & .68 \\ 28 & .41 \\ 35 & .29 \\ 42 & .22 \\ 49 & .22 \\ 56 & .21 \\ 63 & .20 \\ 70 & .19 \end{pmatrix} \quad \mu abs100 := \begin{pmatrix} 10 & 4.3 \\ 20 & .69 \\ 30 & .34 \\ 40 & .25 \\ 50 & .22 \\ 60 & .20 \\ 70 & .19 \\ 80 & .18 \\ 90 & .17 \\ 100 & .17 \end{pmatrix} \quad \mu abs150 := \begin{pmatrix} 15 & 1.4 \\ 30 & .34 \\ 45 & .23 \\ 60 & .20 \\ 75 & .19 \\ 90 & .17 \\ 105 & .16 \\ 120 & .16 \\ 135 & .15 \\ 150 & .15 \end{pmatrix}$$

$$Mnorm100_k := \frac{M100_{k,0}}{\sum_k M100_{k,0}} \quad Mnorm150_k := \frac{M150_{k,0}}{\sum_k M150_{k,0}}$$

$$Mnorm70_k := \frac{M70_{k,0}}{\sum_k M70_{k,0}} \quad \sum_k Mnorm70_k = 1$$

Mnorm is the normalized spectrum of the incident photons. The distance from the x-ray source to the pin hole is 30 cm, and the maximum area of the breast is 20×20 cm.

The pencil beam moves rapidly in the y direction a distance of 20 cm while the pencil beam moves 1 mm in the x direction. The total time for an exposure, Tx, is 10 seconds, and the time for a single y traversal is Ty. The number of y traversals is 20/Dpix. Thus, Tx=10 sec, ty=(tx×Dpix)/20=0.05 sec and the y velocity, Vy=20/Ty=400 cm/sec.

The matrix below shows the output of a typical x-ray tube as a function of the peak x-ray voltage. The first column is the peak x-ray voltage in kilovolts. The second column is the corresponding emission in R/mA/min at 1 meter from target. The measured radiation exposure, R Roentgens/mA/min, can be found in International Commission on Radiological Protection Publication 60 in R/mA/min at 1 meter from the target.

$$Roentgen := \begin{pmatrix} 20 & .20 \\ 40 & .37 \\ 60 & .61 \\ 80 & .90 \\ 100 & 1.0 \\ 120 & 1.48 \\ 140 & 2.00 \\ 160 & 2.31 \\ 180 & 2.78 \\ 200 & 3.00 \end{pmatrix}$$

Interpolating where necessary from the matrix, Roentgen70=0.75/60 R/sec/mA at 1 meter, Roentgen100=1.00/60 R/sec/mA at 1 meter, and Roentgen150=2.15/60 R/sec/mA at 1 meter. For a Toshiba Rotating anode tube, ROTANODE E7823FX, operating at maximum current for 10 sec, this is converted into output per maximum mA as follows: I70=430 mA (30.1 kW), I100=320 mA (32.0 kW), and I150=170 mA (25.5 kW). The present invention contemplates that output power as low as 10 kW is adequate and is defined as a high-power x-ray source.

So the emission from the x-ray tube, R70, with the dimensions of the present system and Tx=10 sec is as follows:

$$R70 = Roentgen70(100/30)^2 \times I70 \times Tx = 597.22 \; Rs;$$

$$R100 = Roentgen100(100/30)^2 \times I100 \times Tx = 592.59 \; Rs;$$

$$R150 = Roentgen150(100/30)^2 \times I150 \times Tx = 676.85 \; Rs;$$

where Rs is the roentgens at the surface of the template 30 cm from the x-ray source and with a total time of exposure of Tx=10 seconds.

Apen=4Apix cm²=4×0.01=0.04 cm² is the area of the pencil beam. This is four times the area of a pixel as the Nyquist theorem is applied. R70 is the entrance exposure to the area of the region used to form the pencil beam of x-rays for a 70 keV x-ray source. Assume that the total area 20×20 cm. Rpb is the flux delivered to the surface of the breast via the pencil beam, and Tpb is the time for a single exposure of each area behind the pinhole and is Tpb=Tx (Apen/20²)=1×10⁻³ sec.

So the entrance exposure is Rpb70=R70(Apen/202)=0.06 Roentgens; Rpb100=R100(Apen/202)=0.06 Roentgens; and Rpb150=R150(Apen/202)=0.07 Roentgens. This is about 1/10 the skin entrance exposure received from a conventional mammogram.

The number of photons, Mphot70, at 30 cm is $$Nphot70_k := \frac{R70 \cdot 2.15 \cdot 10^9}{.07} \cdot Mnorm70_k$$

$$Nphot100_k := \frac{R100 \cdot 2.15 \cdot 10^9}{.1} \cdot Mnorm100_k$$

$$Nphot150_k := \frac{R150 \cdot 2.15 \cdot 10^9}{.150} \cdot Mnorm150_k$$

in photons/cm²/sec/in each energy interval.

$$Nphotsample70_k := Apen \cdot Nphot70_k \cdot Tpb$$

$$Nphotsample100_k := Apen \cdot Nphot100_k \cdot Tpb$$

$$Nphotsample150_k := Apen \cdot Nphot150_k \cdot Tpb$$

in photons/sample/energyinterval. The total number of photons per pencil beam, Nphottot, is $$Nphotsampletot70 := \sum_k Nphotsample70_k$$

$$Nphotsmapletot70 = 7.34 \times 10^8$$

$$Nphotsampletot100 := \sum_k Nphotsample100_k$$

$$Nphotsmapletot100 = 5.1 \times 10^8$$

$$Nphotsampletot150 := \sum_k Nphotsample150_k$$

$$Nphotsampletot150 = 3.88 \times 10^8$$

in photons incident/pencil beam/sample. And the number of photons at each energy interval that reach the depth Xnormal in the absence of a tumor without interaction is Npbnormal.

$$Npbnorm150_{k,r} := (Nphotsample150_k \cdot e^{-Xnorm_r \mu att150_{k,1}})$$

$$Npbnorm70_{k,r} := (Nphotsample70_k \cdot e^{-Xnorm_r \mu att70_{k,1}})$$

$$Npbnorm100_{k,r} := (Nphotsample100_k \cdot e^{-Xnorm_r \mu att100_{k,1}})$$

$$\mu e70 := \begin{pmatrix} .007 & 68 \\ .014 & 60 \\ .021 & 57 \\ .028 & 54 \\ .035 & 50 \\ .042 & 48 \\ .049 & 46 \\ .056 & 44 \\ .063 & 42 \\ .07 & 40 \end{pmatrix} \cdot 10^{-27} \; \mu e100 :=$$

$$\begin{pmatrix} .01 & 64 \\ .02 & 58 \\ .03 & 53 \\ .04 & 49 \\ .05 & 45 \\ .06 & 43 \\ .07 & 40 \\ .08 & 38 \\ .09 & 42 \\ .1 & 38 \end{pmatrix} \cdot 10^{-27} \; \mu e150 := \begin{pmatrix} .015 & 59 \\ .030 & 58 \\ .045 & 57 \\ .060 & 53 \\ .075 & 50 \\ .090 & 42 \\ .105 & 36 \\ .120 & 34 \\ .135 & 33 \\ .15 & 31 \end{pmatrix} \cdot 10^{-27}$$

where column 1 is energy of the incident photon and column 2 is the cross-section for backscatter of the incident photon in cm² per electron×10⁻²⁷. The number of photons scattered into the backscatter detector from the breast after the incident beam has traversed a thickness of, X in the sample is Nback70.

Eff=0.6 is the approximate efficiency of the backscatter detector in detecting single photons. The efficiency to detect a tumor due to the slight difference of density of a tumor is calculated.

Assuming that there is no tumor, Nbacknormal is the number of photons scattered back from the depth r along the pencil beam, of normal tissue:

$$Nbacknorm70_r :=$$

$$\sum_k Npbnorm70_{k,r} \cdot \Omega fix \cdot .1 \cdot \mu e70_{k,1} \cdot eff \cdot Ne \cdot \sum_{s=0}^{9} e^{-Xslant_{r,s} \cdot \mu bs70_{k,1}}$$

$$Nbacknorm100_r :=$$

$$\sum_k Npbnorm100_{k,r} \cdot \Omega fix \cdot .1 \cdot \mu e100_{k,1} \cdot eff \cdot Ne \cdot \sum_{s=0}^{4} e^{-Xslant_{r,s} \cdot \mu bs100_{k,1}}$$

$$Nbacknorm150_r :=$$

$$\sum_k Npbnorm150_{k,r} \cdot \Omega fix \cdot .1 \cdot \mu e150_{k,1} \cdot eff \cdot Ne \cdot \sum_{s=0}^{4} e^{-Xslant_{r,s} \cdot \mu bs150_{k,1}}$$

The number of photons that are scattered backwards into the backscatter detectors is now calculated. It is assumed that the backscattered photons are scattered backwards by an angle of 180°±about 60°. The American Institute of Physics Handbook, Third Edition, Table 8e-1 Collision Differential Cross Sections, at 8-195, has the relevant differential cross-sections, µe, in steradians per electron as a function of angle and incident photon energy. It is shown there that µe is constant over the relevant angles to a good approximation for each of the photon energies of interest. It also lists the energy of the backscattered photon as a function of the energy of the incident photon and the angle of the backscattered photon. There is little change in energy of the scattered photon for any of the energies of the x-rays that are relevant to the present calculation.

It is assumed the tumor begins at depth r1=41 mm and ends at depth r2=50 mm, that is, a tumor with a thickness of 1 g/cm² at the back of the breast. The number of photons scattered back from the pencil beam that includes a portion of the tumor at a depth r is A+B+C, where A is the number scattered back from the normal tissue in front of the tumor (r<r1), B is the number scattered back from the tumor tissue (r1<r<r2), and C is the number scattered back from the normal tissue behind the tumor (r>r2).

$$A70_r := \sum_k Npbnorm70_{k,r} \cdot \Omega fix \cdot .1 \cdot \mu e70_{k,1} \cdot eff \cdot Ne \cdot \sum_{s=0}^{9} e^{(-Xslant_{r,s}) \cdot (\mu bs70_{k,1})}$$

$$B70_r := \sum_k Npbnorm70_{k,r1} \cdot e^{-Xtum_{r-r1} \cdot (\mu att70_{k,1})} \cdot \Omega fix \cdot .1 \cdot \rho tum \cdot \mu e70_{k,1} \cdot eff \cdot Ne \cdot \sum_{s=0}^{9} e^{(-Xslant_{r,s}) \cdot (\mu bs70_{k,1})}$$

$$C70_r := \sum_k \left[ Npbnorm70_{k,r1} \cdot e^{-Xtum_{r2-r1} \cdot (\mu att70_{k,1})} \right] \cdot e^{-Xnorm_{r-r2} \cdot (\mu att70_{k,1})} \cdot \Omega fix \cdot .1 \cdot \mu e70_{k,1} \cdot eff \cdot Ne \cdot \sum_{s=0}^{9} e^{(-Xslant_{r,s}) \cdot (\mu bs70_{k,1})}$$

so Nbacktumtotal is $$Nbacktum70total := \sum_{r=0}^{r1-1} A70_r + \sum_{r=r1}^{r2} B70_r + \sum_{r=r2+1}^{74} C70_r$$

$$Nbacktum70total = 3.3703 \times 10^7$$

$$Nbacknorm70total := \sum_{r=0}^{74} Nbacknorm70_r$$

$$Nbacknorm70total = 3.36953 \times 10^7$$

The difference between the two regions, Δ70total=Nbacktum70total−Nbacknorm70total=7.72×10³ photons/pixel. Note that the relative difference in the observed signal: Δ70total/Nbacknorm70total=2.29×10⁻⁴ is approximately 2 parts in 10,000. A 16-bit detection system will detect the small density differences per pixel.

The standard deviation in the signal from normal tissue is SDNbacknorm70total=√Nbacknorm70total=5.8×10³ photons/pixel and the standard deviation from tumor tissue is SDNbacktum70total=√Nbacktum70total=5.81×10³ photons/pixel.

nSD70 is the number of standard deviations per pixel between the tumor tissue and the normal tissue and is NSD70=Δ70total/SDNbacknorm70total=1.33 standard deviations/pixel. For a 1 cm thick tumor, the number of standard deviations per pixel is as follows:

| Depth (mm) | nSD70 |
|---|---|
| 1-10 | 15.9 |
| 18-27 | 5.1 |
| 35-44 | 1.9 |
| 41-50 | 1.3 |
| 52-61 | 0.8 |

For a peak energy of 100 keV:

$$\rho tum = 1.01$$

$$r := 0 \ldots r1-1$$

$$A100_r := \sum_k Npbnorm100_{k,r} \cdot \Omega fix \cdot .1 \cdot \mu e100_{k,1} \cdot eff \cdot Ne \cdot \sum_{s=0}^{4} e^{(-Xslant_{r,s}) \cdot (\mu bs100_{k,1})}$$

$$r := r1 \ldots r2$$

$$B100_r := \sum_k Npbnorm100_{k,r1} \cdot e^{-Xtum_{r-r1} \cdot (\mu att100_{k,1})} \cdot \Omega fix \cdot .1 \cdot \rho tum \cdot \mu e100_{k,1} \cdot eff \cdot Ne \cdot \sum_{s=0}^{4} e^{(-Xslant_{r,s}) \cdot (\mu bs100_{k,1})}$$

$$r := r2+1 \ldots 74$$

$$C100_r := \sum_k \left[ Npbnorm100_{k,r1} \cdot e^{-Xtum_{r2-r1} \cdot (\mu att100_{k,1})} \right] \cdot e^{-Xnorm_{r-r2} \cdot (\mu att100_{k,1})} \cdot \Omega fix \cdot .1 \cdot \mu e100_{k,1} \cdot eff \cdot Ne \cdot \sum_{s=0}^{4} e^{(-Xslant_{r,s}) \cdot (\mu bs100_{k,1})}$$

so Nbacktumtotal is $$Nbacktum100total := \sum_{r=0}^{r1-1} A100_r + \sum_{r=r1}^{r2} B100_r + \sum_{r=r2+1}^{74} C100_r = 1.64497 \times 10^7$$

$$Nbacknorm100total := \sum_{r=0}^{74} Nbacknorm100_r = 1.64 \times 10^7$$

The difference between the two regions is Δ100total=Nbacktum100total−Nbacknorm100total=5.32×10³ photons/pixel. Note that the relative difference in the observed signal: Δ100total/Nbacknorm100total=3.23×10⁻⁴ is approximately 3 parts in 10,000. A 16-bit detection system will detect the small density differences per pixel.

The standard deviation in the signal from normal tissue is SDNbacknorm100total=√Nbacknorm100total=4.06×10³ photons/pixel and the standard deviation from tumor tissue is SDNbacktum100total=√Nbacktum100total=4.06×10³ photons/pixel.

nSD100 is the number of standard deviations per pixel between the tumor tissue and the normal tissue and is NSD100=Δ100total/SDNbacknorm100total=1.31 standard deviations/pixel. For a 1 cm thick tumor, the number of standard deviations per pixel is as follows:

| Depth (mm) | nSD100 |
|---|---|
| 1-10 | 9.6 |
| 18-27 | 3.7 |
| 35-44 | 1.7 |
| 41-50 | 1.3 |
| 52-61 | 0.9 |

For a peak energy of 150 keV:

$r := 0 \ldots r1 - 1$ $$A150_r := \sum_k Npbnorm150_{k,r} \cdot \Omega fix \cdot .1 \cdot \mu e150_{k,1} \cdot$$

$$eff \cdot Ne \cdot \sum_{s=0}^{4} e^{(-Xslant_{r,s}) \cdot (\mu bs150_{k,1})}$$

$r := r1 \ldots r2$ $$B150_r := \sum_k Npbnorm150_{k,r1} \cdot e^{-Xtum_{r-r1} \cdot (\mu att150_{k,1})} \cdot$$

$$\Omega fix \cdot .1 \cdot \rho tum \cdot \mu e150_{k,1} \cdot eff \cdot Ne \cdot \sum_{s=0}^{4} e^{(-Xslant_{r,s}) \cdot (\mu bs150_{k,1})}$$

$r := r2 + 1 \ldots 74$ $$C150_r :=$$

$$\sum_k \left[ Npbnorm150_{k,r1} \cdot e^{-Xtum_{r2-r1} \cdot (\mu att150_{k,1})} \right] \cdot e^{-Xnorm_{r-r2} \cdot (\mu att150_{k,1})} \cdot$$

$$\Omega fix \cdot .1 \cdot \mu e150_{k,1} \cdot eff \cdot Ne \cdot \sum_{s=0}^{4} e^{(-Xslant_{r,s}) \cdot (\mu bs150_{k,1})}$$

so Nbacktumortotal is $$Nbacktum150total := \sum_{r=0}^{r1-1} A150_r + \sum_{r=r1}^{r2} B150_r + \sum_{r=r2+1}^{74} C150_r = 1.68679 \times 10^7$$

$$Nbacknorm150total := \sum_{r=0}^{74} Nbacknorm150_r = 1.68612 \times 10^7$$

The difference between the two regions is Δ150total=Nbacktum150total−Nbacknorm150total=6.76× $10^3$ photons/pixel. Note that the relative difference in the observed signal: Δ150total/Nbacknorm150total=4.01×10$^{-4}$ is approximately 4 parts in 10,000. A detection system that can detect one photon out of $2^{12}$ photons, i.e., a 12-bit detection system, will detect the small density differences per pixel.

The standard deviation in the signal from normal tissue is SDNbacknorm150total=√Nbacknorm150total=4.11×10$^3$ photons/pixel and the standard deviation from tumor tissue is SDNbacktum150total=√Nbacktum150total=4.11×10$^3$ photons/pixel.

nSD150 is the number of standard deviations per pixel between the tumor tissue and the normal tissue and is NSD150=Δ150total/SDNbacknorm150total=1.65 standard deviations/pixel. For a 1 cm thick tumor, the number of standard deviations per pixel is as follows:

| Depth (mm) | nSD150 |
|---|---|
| 1-10 | 9.1 |
| 18-27 | 4.2 |
| 35-44 | 2.1 |
| 41-50 | 1.6 |
| 52-61 | 1.1 |

Figure 8:
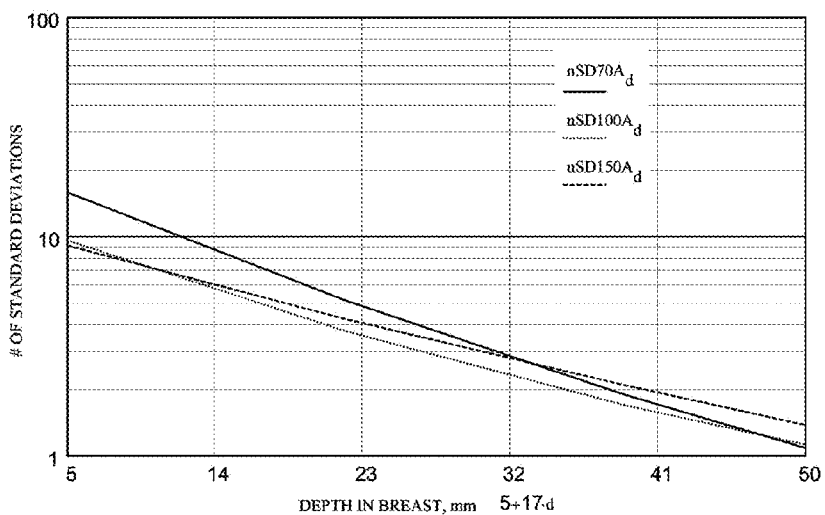
FIG. 8 is a graph of the contrast versus depth for each peak energy.

A graph of the contrast versus depth for each peak energy is shown in FIG. 8.

Thus, for an x-ray tube operating at 70, 100, and 150 keV and a tube current of 170 mA, an assumed difference in density between tumor tissue and normal tissue of 1%, an examination time of 10 seconds for a 20 cm×20 cm area of breast, an entrance exposure of less than 70 milliroentgens, a pixel size of 1 mm, and a 1 cm thick tumor in the back of a 5 cm breast, the number of standard deviations (contrast) between tumor tissue and normal tissue is 1.3, 1.3, and 1.6 standard deviations, respectively, per pixel at a depth of 5 cm in the breast and the number of standard deviations between tumor tissue and normal tissue is 15.9, 9.6, and 9.1, respectively, per pixel just below the surface of the breast. Thus detailed spatial studies may be made of the tumor structure.

Figure 5:
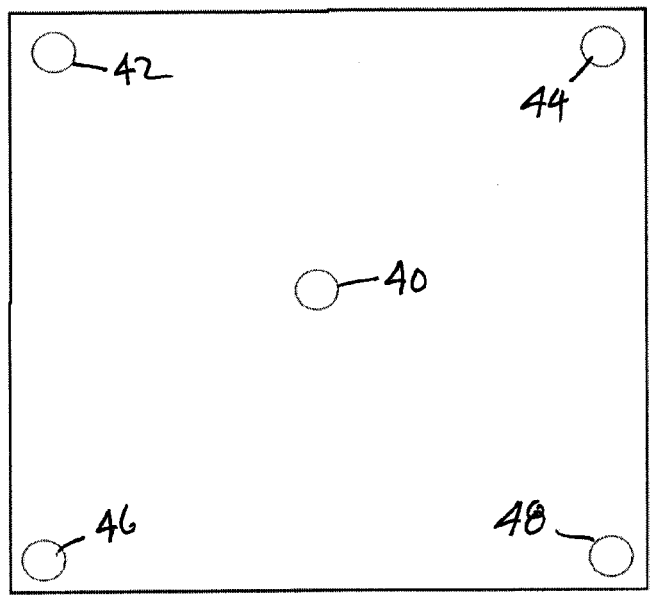
FIG. 5 is schematic showing several positions for the x-ray source to use the present system to produce three-dimensional tomography images.

FIG. 5 shows a version of the present invention that can be used to produce three-dimensional tomography images. After an x-ray backscatter image is produced with the x-ray source 12 in the central position 40 relative to the disc slots 16 and plate slit 20, another backscatter image is produced after moving the x-ray source 12 to at least one of the other positions 42, 44, 46, 48. Preferably, four other positions 42, 44, 46, 48 are used. Thus, five backscatter images are produced of the object. These five images are combined by the usual procedure to produce digital tomography images of "slices" parallel to the surface of the object at different depths within the object being scanned. The algorithm may be any one of a number of well-known algorithms used in combining multiple transmission images.

This is the first method, or at least the first practical method, of producing three-dimensional digital tomography images that uses blurring in two orthogonal directions. All previous systems move the x-ray source substantially in a plane perpendicular to the surface of the object and/or in a straight line or in an arc of a circle. Blurring in two orthogonal directions removes many of the artifacts found in all prior art systems.

Thus it has been shown and described an x-ray backscatter system for imaging soft tissue which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

What is claimed is:

1. A backscatter scan system for imaging a soft tissue region of an object, said system comprising:
    (a) in order from back to front, a high power x-ray source emitting a cone beam with an axis, a rotating x-ray blocking disk having a plurality of radial disc slots and rotating perpendicularly to said cone beam axis, an x-ray blocking plate with a plate slit, an x-ray detector with a detector slit that is slightly larger than and aligned with said plate slit, and an object space having a length and a width and adapted to receive said object;
    (b) said x-ray source emitting said cone beam to said disc with a peak energy of greater than 50 keV, said disc slots emitting a moving fan beam to said plate, said plate slit emitting a scanning pencil beam as said disc slots traverse said plate slit, said pencil beam passing through said detector slit into said object space;

(c) an assemblage of said x-ray source, said disk, said plate, and said detector moving slowly in a first direction said width of said object space;

(d) said pencil beam traversing across said object space in a line in a second direction and for a distance equal to said length of said object space, said second direction being generally orthogonal to said first direction, said pencil beam traversing said object space a plurality of times in a plurality of said lines as said assemblage moves said width of said object space;

(e) said detector receiving backscattered x-rays from said object space to produce a plurality of line signals from said plurality of pencil beam lines; and (f) a processor that forms a plurality of line images from said plurality of line signals.

2. The backscatter scan system of claim 1 wherein said soft tissue region is a human breast and said breast is compressed into the chest during imaging.

3. The backscatter scan system of claim 1 wherein said object area is approximately 20 cm long, approximately 20 cm wide, and approximately 5 cm deep, the distance from said x-ray source to said disc is at least 30 cm, and said pencil beam is approximately 2 mm by 2 mm in cross-section.

4. The backscatter scan system of claim 3 wherein said pencil beam scans one line in 0.1 sec and said assemblage moves said width of said object space in approximately 10 sec.

5. The backscatter scan system of claim 1 wherein said x-ray source is of the rotating anode type.

6. A method of imaging a human breast comprising the steps of:

(a) providing, in order from back to front, a high power x-ray source, a rotating x-ray blocking disk having a plurality of radial disc slots and rotating perpendicularly to said cone beam axis, an x-ray blocking plate with a plate slit, an x-ray detector with a detector slit that is slightly larger than and aligned with said plate slit, and an object space having a length and a width and adapted to receive said breast;

(b) compressing said breast against the chest in said object space;

(c) said x-ray source emitting a cone beam to said disc with a peak energy of greater than 50 keV, said disc slots emitting a moving fan beam to said plate, said plate slit emitting a scanning pencil beam as said disc slots traverse said plate slit, said pencil beam passing through said detector slit into said object space;

(d) moving an assemblage of said x-ray source, said disk, said plate, and said detector slowly in a first direction said width of said object space;

(d) said pencil beam traversing across said object space in a line in a second direction and for a distance equal to said length of said object space, said second direction being generally orthogonal to said first direction, said pencil beam traversing said object space a plurality of times in a plurality of said lines as said assemblage moves said width of said object space;

(e) said detector receiving backscattered x-rays from said object space to produce a plurality of line signals from said plurality of pencil beam lines; and (f) forming a plurality of line images of said breast from said plurality of line signals.

7. The method of claim 6 wherein said object area is approximately 20 cm long, approximately 20 cm wide, and approximately 5 cm deep, the distance from said x-ray source to said disc is at least 30 cm, and said pencil beam is approximately 2 mm by 2 mm in cross-section.

8. The method of claim 7 wherein said pencil beam scans one line in 0.1 sec and said assemblage moves said width of said object space in approximately 10 sec.

9. The method of claim 6 wherein said x-ray source is of the rotating anode type.

* * * * *